United States Patent [19]
Alicot et al.

[11] 4,371,698
[45] Feb. 1, 1983

[54] PROCESS FOR THE PURIFICATION OF MERCAPTOBENZOTHIAZOLE

[75] Inventors: Michel J. C. Alicot, La Barthe De Neste; Adrien P. N. Tignol, Montrejeau, both of France

[73] Assignee: P C U K Produits Chimiques Ugine Kuhlmann, Courbevoie, France

[21] Appl. No.: 121,570

[22] Filed: Feb. 14, 1980

[30] Foreign Application Priority Data

Mar. 6, 1979 [FR] France ................. 79 05710

[51] Int. Cl.³ .......................... C07D 277/72
[52] U.S. Cl. .................... 548/177; 548/166
[58] Field of Search ................ 548/177, 176

[56] References Cited

U.S. PATENT DOCUMENTS 2,090,233  8/1937  Roberts ................. 548/177
2,161,741  6/1939  Gage ................... 548/177
4,192,804  1/1980  Alicot et al. ........... 548/177

FOREIGN PATENT DOCUMENTS 2397409  2/1979  France .

OTHER PUBLICATIONS

A. Weissberger, "Technique of Org. Chem., vol. III, Part I Sep. & Purif", pp. 742-744, (1956) Interscience, NY.

Primary Examiner—Donald G. Daus
Assistant Examiner—D. B. Springer
Attorney, Agent, or Firm—Beveridge, DeGrandi & Kline

[57] ABSTRACT

Process for the purification of mercaptobenzothiazole in which the crude product resulting from the reaction of aniline, sulfur and carbon disulfide according to the known process is treated with aniline.

7 Claims, No Drawings

PROCESS FOR THE PURIFICATION OF MERCAPTOBENZOTHIAZOLE

Mercaptobenzothiazole is known for its use as a vulcanization accelerator in the industry for the conversion of elastomers. It is also a very important material in the synthesis of improved vulcanization accelerators, adapted to the particular problems which arise in the manufacture of articles as different as, for example, pneumatic parts, electric cables, footwear soles and insulation joints. It also enters in a significant way into the synthesis of pesticides.

Most of the known manufacturing processes for mercaptobenzothiazole make use of the reaction, in suitable proportions and at high temperature and high pressure, of aniline, sulfur and carbon disulfide. Other processes make use either of the reaction of thiocarbanilide, carbon disulfide and sulfur (U.S. Pat. No. 1,712,968 dated May 14, 1929) or the reaction of orthochloronitrobenzene, hydrogen sulfide or an alkali metal sulfide and carbon disulfide (U.S. Pat. No. 1,960,205 dated May 22, 1934, Polish Pat. No. 86988 of Dec. 15, 1976), or also the reaction of benzothiazole and sulfur (German Pat. No. 2,551,060 of May 26, 1976). The reaction product obtained under such conditions is never directly utilizable as such. It contains, in fact, unreacted starting materials, for example aniline, by-products and intermediates such as benzothiazole and anilinobenzothiazole. A careful purification of the crude reaction product is necessary.

To data, numerous processes of purification have been proposed. Fundamentally, three techniques are used which differ chiefly in the concentrations, the order of use, the nature of the recommended reactants and the temperatures of treatment.

The scheme of the principle of the first technique is as follows:

(a) Solubilization of the reaction product in alkaline medium (ammonium hydroxide, sodium hydroxide, calcium hydroxide) which may or may not be preceded by a treatment in inorganic acid medium;

(b) Separation of the insoluble impurities by filtration;

(c) Separation of the soluble impurities after their insolubilization by oxidation and/or extraction with a solvent;

and (d) Precipitation of the mercaptobenzothiazole by the action of an inorganic acid.

U.S. Pat. Nos. 1,631,871, 2,658,864, 2,730,528 and 3,818,025 and French Pat. No. 2,135,807 illustrate the application, wholly or in part, of such a process.

In the second technique, the impurities are extracted by treatment of the reaction product with carbon disulfide or an emulsion of carbon disulfide and water. U.S. Pat. Nos. 2,090,233, 3,030,373 and 3,031,073 illustrate this second method.

Although they may actually be industrialized, these processes are not satisfactory and each shows wholly or in part the following disadvantages:

1. Difficult recovery of the unreacted starting materials which it is of the greatest economic interest to recycle (aniline in particular).

2. The need to operate at less than high concentrations in order to favor the precipitation of the impurities with, in consequence, apparatus of large dimensions.

3. Losses by chemical degradation of mercaptobenzothiazole during the oxidation reactions intended to insolubilize the soluble impurities in alkaline medium.

4. Losses by solubilization of mercaptobenzothiazole in the carbon disulfide or inevitable recycling of a part of the impurities if the amount of carbon disulfide is limited. A supplementary disadvantage is the necessity of handling large amounts of this highly inflammable reagent.

5. Finally, and this is perhaps the major disadvantage of these processes, the necessity of having to treat before their rejection large volumes of aqueous effluents containing strong polluting charges. These treatments are difficult and costly. The processes of oxidation generally applied do not lead to the desired simple molecules of nitrogen, carbon dioxide and sulfur dioxide, but to an unacceptable ratio of soluble molecules which are only degraded by a complementary biological treatment which heavily increases the cost of the production units and the prime cost.

A third technique takes into account the property of certain solvents to solubilize the impurities contained in the crude reaction product, the mercaptobenzothiazole being itself insoluble in these solvents. This technique has proved very advantageous compared to the preceding techniques because of its simplicity and the yield from purification which can thus be attained. 1,1,2,2-tetrachloro-ethylene and carbon tetrachloride in this capacity are particularly effective solvents (French Pat. No. 2,397,409).

Nevertheless, it may be considered that in spite of the progress which this technique brings with respect to the preceding ones, it necessitates the introduction into the manufacturing process of a supplementary starting material with the consequence that this brings: supplementary stocks, material for recovery.

It has now been found by the applicants that it is possible, from the crude product resulting from the reaction of aniline, sulfur and carbon disulfide at high pressure and high temperature according to the known processes, to obtain the mercaptobenzothiazole with a high yield from purification in a high state of purity, by means of a simplified technique which takes into account the solvent character of one of the reagents in the reaction.

In said known process, the reaction of 93 parts of aniline, 25.6 to 35.2 parts of sulfur and 60.8 to 98.8 parts of carbon disulfide is conducted at a pressure of from 50 to 150 bars and at a temperature of from 200° C. to 300° C. Suitable known processes are described, for example, in the U.S. Pat. Nos. 1,631,871 (June 7, 1927) and 3,818,025 (June 18, 1974), the disclosures of which are incorporated herein by reference in their entireties.

The process according to the present invention for the purification of the mercaptobenzothiazole is characterized in that the crude product resulting from the reaction of aniline, sulfur and carbon disulfide according to the known processes is treated with aniline, a starting material of the reaction.

In carrying out the process of the invention, it is advantageous to operate as follows:

1. Addition of aniline to the product of the reaction;

2. Filtration and washing with aniline of the insolubilized mercaptobenzothiazole; and 3. Recycling of the liquid phase of the purification medium.

STAGE 1

Addition of aniline

The addition of the aniline can be effected in two ways:

1.1—Directly in the synthesis reactor, preferably at the end of the reaction, by any known means (as for example a high pressure dosing pump). The introduction at the head of the reactor is not advised although it may be possible, due to the secondary reactions of the aniline in large excess with the various components of the reaction mixture. The temperature at which the addition of the aniline is effected is between the reaction temperature and the temperature of solidification of the crude product, that is between 170° C. and 300° C. The selected range is preferably 180° C.-220° C.

In this method of operation, the temperature of the reaction mixture upon releasing it to atmospheric pressure may be distinctly lower than the solidification temperature thereof. It is only a function of the quantity of aniline with respect to with the degree of solubility of the mercaptobenzothiazole in this solvent.

1.2—The addition of aniline may be effected by another variant: by mixing with the crude reaction product, after releasing it to atmospheric pressure; preferably the gaseous by-products such as hydrogen sulfide are previously separated by known degassing procedures.

In this case the temperature of mixing is between the ambient temperature and the boiling temperature of the aniline, i.e. between 15° C. and 184° C.

Before effecting the filtration, and so that the solubilization of the impurities and the washing may be effective, it is preferable that in the reaction mixture diluted with aniline and preferably brought to the ambient temperature, the insolubilized mercaptobenzothiazole particles should be fine-grained. Although it is not restrictive, a value less than 100 microns is considered as satisfactory. This result is easily obtained by any known means.

STAGE 2

Filtration—Washing

The filtration and washing in aniline of the precipitated mercaptobenzothiazole is effected according to conventional methods well known to one skilled in the art. The amount of aniline used is linked to the efficiency of the technological means employed. The elimination of the aniline contained in the drained filter cake after washing may be effected by the method of removal by steam or evaporation under vacuum. It is preferred to use the latter. When used continuously, it simplifies the recovery of the aniline and above all avoids any aqueous effluent.

STAGE 3

Recycling

The recycling of the liquid phases is carried out after the aniline is distilled whereby it is concentrated to a determined volume (linked to that in which one chooses to operate solubilization of the impurities), and after the removal of a volume calculated so that there may be eliminated in unit time a weight of impurity equal to that provided by the reaction product.

This assumes that previously, in a period of putting into operation, the recycling of the liquid phases is effected a certain number of times without removal. In this way the amount of impurities becoming sufficiently high with respect to that of the solubilized mercaptobenzothiazole, the losses in this latter product in the purification become economically acceptable. Although the process with the three stages above is the preferred process, one will not depart from the framework of the invention by refraining from recycling the liquid phases.

The process of the invention allows the recovery without difficulty of the unreacted starting material and the valuable by-products found in the reaction product: aniline and benzothiazole in particular. This recovery is made on the one hand during the concentration of the liquid phases before recycling, and on the other hand by distillation of the removed fraction.

Since it offers the possibility of obtaining purification of the mercaptobenzothiazole without having recourse to an aqueous phase, the process of the invention substantially abolishes the problems caused by the treatment of effluents of this type of industrial installation.

The following example illustrates the invention without it being restricted thereto. In the example and throughout the specification and claims, all parts and percentages are by weight unless otherwise specified.

EXAMPLE

This example describes the purification of the mercaptobenzothiazole by means of aniline after the period of putting into operation (see above stage 3). Putting the purification medium in a state of equilibrium is effected by a series of recyclings of the whole of the impurities to be eliminated, so that the amount of impurities is sufficiently increased.

1000 grams of liquid phase from a prior operation of purification of mercaptobenzothiazole, composed of 50.7% of aniline, 1.24% of benzothiazole, 18.8% of mercaptothiazole and 29.25% of various by-products, are introduced into a reactor provided with an emulsifier agitator (i.e. Rayneri type) and a temperature probe.

400 grams of reaction mixture resulting from the reaction of sulfur, aniline, and carbon disulfide having the composition: 2.75% of aniline 5% of benzothiazole, 83.25% of mercaptobenzothiazole and 9% of various by-products, withdrawn at a temperature of 180° C. from a reactor for synthesis of mercaptobenzothiazole, and after removal of hydrogen sulfide by degassing, are then introduced with vigorous agitation.

Vigorous agitation is continued for about an hour at the temperature of 20° C. to 25° C. The grain size of the insolubilized particles of mercaptobenzothiazole is of the order of 40 to 60 microns.

The mixture is filtered and the product on the filter is washed with 1100 grams of aniline several times and drained.

The filter cake obtained having a weight of about 700 grams is subjected to evaporation under vacuum (about 15 to 20 mm Hg) at a temperature of 100° C. to 110° C., while lightly flushing the cake with nitrogen. 329 grams of purified mercaptobenzothiazole are obtained of titre 98.8% and melting point (uncorrected) of 177°-180° C.

The yield from the purification is 97.6%.

The filtrate from the filtration, after elimination of 90 grams, is added to the various fractions from the washing: after concentration to 1000 grams by distillation under reduced pressure, it is recycled in a further purification operation.

The purge or amount removed from the filtrate which contains 8.9% of mercaptobenzothiazole, which value represents about 8 grams or 2.4% of the amount of mercaptobenzothiazole introduced, is distilled under vacuum so as to recover the aniline and the benzothiazole. The undistillable part is either eliminated or recycled wholly or in part in the synthesis reactor.

What is claimed is:

1. Process for the purification of mercaptobenzothiazole which comprises the steps of adding aniline to the crude product resulting from the reaction of aniline, sulfur and carbon disulfide in the reactor where the synthesis took place, at a temperature between 170° and 300° C., the amount of aniline being sufficient to solubilize the impurities in said crude product, cooling the resultant mixture to ambient temperature, filtering and washing with aniline the precipitated mercaptobenzothiazole which is thus obtained as a purified product.

2. Process as claimed in claim 1 in which aniline is added at a temperature between 180° C. and 220° C.

3. Process as claimed in claim 1 or 2 in which the mercaptobenzothiazole particles of said mixture brought to ambient temperature have a size less than 100 microns before effecting the filtration.

4. Process as claimed in claim 1 or 2 in which the aniline used for purification consists essentially of aniline recovered from the washed cake of mercaptobenzothiazole by evaporation under vacuum.

5. Process as claimed in claim 1 or 2 in which the aniline used for purification consists essentially of aniline recovered from fractions from the washing by distillation.

6. Process for the purification of mercaptobenzothiazole which comprises the steps of releasing the crude product to atmospheric pressure in the reactor where the synthesis took place, removing the gaseous by-product from said crude product resulting from the reaction of aniline, sulfur and carbon dioxide, mixing the degassified product, at a temperature between 15° C. and 184° C., with aniline in sufficient amount to solubilize the impurities in said crude product, cooling the resultant mixture to ambient temperature, filtering and washing with aniline the precipitated mercaptobenzothiazole which is thus obtained as a purified product.

7. Process according to claim 6 in which the degassified product is mixed with aniline at a temperature of 180° C.

* * * * *